(12) United States Patent
Di Rienzo et al.

(10) Patent No.: US 6,472,157 B2
(45) Date of Patent: Oct. 29, 2002

(54) METHODS FOR DETECTION OF PROMOTER POLYMORPHISM IN A UGT GENE PROMOTER

(75) Inventors: Anna Di Rienzo; Lalitha Iyer; Mark J. Ratain, all of Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 10/061,693

(22) Filed: Feb. 1, 2002

(65) Prior Publication Data

US 2002/0115097 A1 Aug. 22, 2002

Related U.S. Application Data

(63) Continuation of application No. 09/251,274, filed on Feb. 16, 1999, now Pat. No. 6,395,481.

(51) Int. Cl.$^7$ ............ C12Q 1/68; C12P 19/34; C07H 21/04; C07H 21/02

(52) U.S. Cl. ............ 435/6; 435/91.1; 435/91.2; 536/22.1; 536/24.3; 536/24.33

(58) Field of Search ............ 435/6, 91.1, 91.2; 536/22.1, 24.3, 24.33

(56) References Cited

U.S. PATENT DOCUMENTS

| 5,786,344 A | 7/1998 | Ratain et al. ............ 514/100 |
| 6,066,645 A | 5/2000 | Hausheer et al. ............ 514/283 |

FOREIGN PATENT DOCUMENTS

| WO | WO 96/01127 | 1/1996 |

OTHER PUBLICATIONS

Araki et al., "Relationship between development of diarrhea and the concentration of SN–38, an active metabolite of CPT–11, in the intestine and blood plasma of athymic mice following intraperitoneal administration of CPT–11," *Jpn J. Cancer Res.*, 84:697–702, 1993.

Beutler et al., "Racial variability in the UDP–glucuronosyltransferase 1 (UGT1A1) promoter: a balanced polymorphism for regulation of bilirubin metabolism," *PNAS USA*, 95:8170–8174, 1998.

Bosma et al., "Sequence of exons and the flanking regions of human bilirubin–UDP–glucuronosyltransferase gene complex and identification of a genetic mutation in a patient with Crigler–Najjar Syndrome, Type I," *Hepatology*, 15:941–947, 1992.

Bosman et al., "The genetic basis of the reduced expression of bilirubin UDP–Glucuronosyltransferase 1 in Gilbert's Syndrome," *N. Eng. J. Med.*, 333:1171–1175, 1995.

Burchell et al., The UDP Glucuronosyltransferase gene suprefamily: suggested nomenclature based on evolutionary divergence, *DNA cell biol.*, 10:487–494, 1991.

Chen et al., "Calcium phosphate–mediated gene transfer: A highly efficient transfection system for stably transforming cells with plasmid DNA," *Biotechniques*, 6:632–638, 1988.

Clarke et al., "The Uridine Diphosphate glucuronosyltransferase multigene family: function and regulation," *Handbook of experimental pharmacology*, 112:3–43, 1994.

Coffman et al., "Cloning and stable expression of a cDNA encoding a rate liver UDP–Glucuronosyltransferase (UDP_Glucuronosyltransferase 1.1) that catalyzes the glucuronidation of opiods and bilirubin," *Mol. Pharmacol.*, 47:1101–1105, 1995.

Coffman et al., "Human UGT2B7 catalyzes morphine glucuronidation," *Drug Metab Dispos.*, 25:1–4, 1997.

Di Rienzo et al., "Two new alleles in the promoter of the bilirubin UDP–glucuronosyl transferase 1 (UGT1A1) gene", *American Society for Clinical Pharmacology and Therapeutics*, Ninety Ninth Annual Meeting, New Orleans, Abstract OII–B–3, p. 207, 1998.

Evans and Relling, "Automated high–performance liquid chromatographic assay for the determinationof 7–ethoxycoumarin and umbelliferone," *J. Chromatogr.*, 578:141–145, 1992.

Gram et al., "Clinical relevance of gentic polymorphisms in drug oxidation," *Clinical Relevance of Genetic Polymorphisms in Drug Oxidation*, 1992.

Green et al., "Expressed human UGT1.4 protein catalyzes the formation of quaternary ammonium–linked glucuronides," *Drug Metab. Dispos.*, 23:299–302, 1995.

Gunn,"Hereditary Acholuric Jaundice," *J. Hered.*, 29:137–139, 1938.

Gupta et al., "Metabolic Fate of Irinotecan in humans: Correlation of Glucuronidation with Diarrhea," *Cancer Res.*, 54:3723–3725, 1994.

Gupta et al., "Pharmacokinetic and pharmacodynamic evaluation of the topisomerase inhibitor Irinotecan in cancer patients," *J. Clin. Oncol.*, 15:1502–1510, 1997.

Harding et al., "Cloning and substrate specificity of a human phenol UDP–glucuronosyltransferase expressed in COS–7 cells," *PNAS, USA*, 85:8381–8385, 1988.

(List continued on next page.)

Primary Examiner—W. Gary Jones
Assistant Examiner—Arun Kv. Chakrabarti
(74) Attorney, Agent, or Firm—Fulbright & Jaworski (57) ABSTRACT

The present invention is directed to methods for detecting the presence of genetic polymorphisms that correlate with altered gene expression. More specifically, the present invention is directed to methods for detecting the genetic polymorphisms located in the UGT1A1 promoter. The invention also provides methods for optimizing drug dosages based upon the presence of the polymorphisms. The invention further provides methods of predicting sensitivity to xenobiotics and diagnostic kits for detecting genetic polymorphisms.

26 Claims, 1 Drawing Sheet

OTHER PUBLICATIONS

Iyer et al., "Genetic basis for the glucuronidation of SN–38: Role of UGT*1 isoform," *Clinical Pharmacology and Therapeutics*, 61:Abstract, 1997.

Iyer et al., "UGT isoform 1.1 (UGT*1.1) glucuronidates SN–38, the active metabolite of irinotecan," *Program Proceedings of the American Society of Clinical Oncology*, 16:Abstract, 1997.

Kaneda et al., "Metabolism and Pharmacokinetics of the campothecin analogue CPT–11 in the mouse," *Cancer Res.*, 50:1715–1720, 1990.

King et al., "The Glucuronidation of exogenous and endogenous compounds by stably expressed rat and human UDP–Glucuronosyltransferase 1.1," *Arch. Biochem. Biophys.*, 332:92–100, 1996.

Monaghan et al., "Genetic variation in bilirubin UDP-glucuronosyltransferase gene promoter and Gilbert's syndrome," *Lancet*, 347:578–581, 1996.

Owens and Ritter, "Gene structure at the human UGT1 locus creates diversity in isozyme structure, substrate specificity and regulation," *Progress in Nucleic Acid Research and Molecular Biology*, 51:305–338, 1995.

Purba et al., "The metabolism of 17 α–ethinyloestradiol by human liver microsomes: formation of catechol and chemically reactive metabolites," *Br. J. Clin. Pharmacol.*, 23:447–453, 1987.

Ritter et al., "A novel complex locus UGT1 encodes human bilirubin, phenol and other UDP–glucuronosyltransferase isozymes with identical carboxyl termini," *J. Biol. Chem.*, 267:3257–3261, 1992.

Ritter et al., "Cloning of two humna liver bilirubin UDP–glucuronosyltransferase cDNAs with expression in COS–1 cells," *J. Biol. Chem.*, 226:1043–1047, 1991.

Stocker, "Bilirubin is an antioxidant of possible physiological importance," *Science*, 235:1043–1046, 1987.

Tucker, "Clinical implications of genetic polymorphism in drug metabolism," *J. Pharm. Pharmacology*, 46:417–424, 1994.

METHODS FOR DETECTION OF PROMOTER POLYMORPHISM IN A UGT GENE PROMOTER

This is a continuation of co-pending application Ser. No. 09/251,274, filed Feb. 16, 1999 now U.S. Pat. No. 6,395,481.

The U.S. Government has a paid-up license in this invention and the right in limited circumstances to require the patent owner to license others on a reasonable terms as provided for by the terms of Grant No. NSF-9317266 awarded by the National Science Foundation.

BACKGROUND

Researchers have invested considerable effort attempting to identify the pharmacogenetic basis of idiosyncratic adverse drug reactions, particularly hypersensitivity reactions. There is clear evidence for pharmacogenetic influence on susceptibility to hypersensitivity reactions. One such pharmacogenetic influence is genetic polymorphism. Genetic polymorphism involve the regular and simultaneous existence in the same population of two or more discontinuous variants or genotypes in frequencies that cannot be due to recurrent mutations. Probably, the best known example of genetic polymorphism involves the different human blood groups. Genetic polymorphism at loci which encode enzymes involved in metabolism of toxic or carcinogenic compounds can have clinical implications in drug metabolism. The pharmacokintetic and pharmacodynamic consequences of the activity of a polymorphic enzyme depend upon whether it mediates metabolism of the parent drug, the metabolites or both, whether parent drug or metabolites or both are active, the overall contribution to clearance from the affected pathway, the potency of the active species, and the patency of competing pathways of elimination. Tucker, *Journal Pharmacology*, 46, 417–424 (1994). Examples of the various permutations have been illustrated by Gram, et al in Clinical Relevance of Genetic Polymorphisms in Drug Oxidation, (1992).

One group of polymorphic enzymes that has implications in drug metabolism is the glucuronosyltransferases. Glucuronosyltransferases (UGTs) are the enzymes responsible for converting endogenous, toxic or carcinogenic compounds into a more water soluble form so they may be excreted from the body. UGTs are members of the transferase class of enzymes and are characterized by their ability to catalyze reactions that transfer functional groups from one compound to another. During metabolism, UGTs render polarity to xenobiotics and other exogenous compounds by catalyzing the transfer of a glucuronate moiety from uridine diphosphate glucuronate to an acceptor β-D-glucuronoside to form a glucuronide conjugate which can then be secreted into the bile. In addition to catalyzing reactions to detoxify exogenous compounds, UGTs catalyze reactions that impart water solubility to endogenous compounds. For example, UGTs catalyze a reaction in the liver whereby bilirubin is rendered water soluble by conjugation to form bilirubin bisglucuronide, most of which is excreted in the bile.

Higher than normal levels of bilirubin in the blood can be caused by one such genetic polymorphism, Gilbert's Syndrome. Gilbert's Syndrome (GS) is a benign unconjugated hyperbilirubinemia characterized by the presence of higher than normal concentrations of bilirubin in the blood. The higher than normal levels of bilirubin in the blood often result in episodes of mild intermittent jaundice. Gilbert's syndrome hyperbilirubinemia occurs in the absence of structural liver disease and overt hemolysis. It is part of a spectrum of familial unconjugated hyperbilirubinemias including the more severe Crigler-Najjar (CN) Syndromes (types 1 and 2). GS is the most common inherited disorder of hepatic bilirubin metabolism occurring in 2–12% of the population and is often detected in adulthood through routine screening blood tests or the fasting associated with surgery or illness which unmasks the hyperbilirubinemia. The most consistent feature in GS is a deficiency in bilirubin glucuronidation but altered metabolism of drugs has also been reported. Altered rates of bilirubin production, hepatic heme production and altered hepatic uptake of bilirubin have been reported in some GS patients. Due to the benign nature of the syndrome and its prevalence in the population it may be more appropriate to consider GS as a normal genetic variant exhibiting reduced bilirubin glucuronidation capacity (which in certain situations such as fasting, illness or administration of drugs) could precipitate jaundice.

In addition to bilirubin metabolism, the glucuronidation detoxification pathway is also responsible for detoxifying many other compounds. For example, two promising anti-tumor agents, Irinotecan (CPT-11) and TAS-103, are detoxified in the liver by the same pathway. While Irinotecan has been recently approved for repeats use in patients with metastatic colorectal cancer, TAS-103 is currently undergoing Phase I clinical trials in the United States. The active metabolite of Irinotecan, SN-38, and TAS-103 are both glucuronidated by hepatic uridine diphosphate glucuronosyltransferases (UGTs) in vivo. The major dose-limiting toxicity of Irinotecan therapy is diarrhea, which is believed to be secondary to the biliary excretion of SN-38, the extent of which is determined by SN-38 glucuronidation. On the other hand, the major toxicity associated with TAS-103 therapy is leukopenia. In the case of both drugs, glucuronidation is the major detoxification pathway. In patients with GS or CN, where glucuronidation activity is low, increased susceptibility to drug toxicity is a major problem. There remains a need in the art for a method to detect genetic polymorphisms at loci which encode enzymes involved in metabolism of endogenous, toxic or carcinogenic compounds.

SUMMARY OF THE INVENTION

The present invention is directed to methods for detecting promoter polymorphisms that correlate with altered gene expression. More specifically, the present invention is directed to methods for determining the presence of genetic polymorphisms within a uridine diphosphate glucuronosyltransferase and or its promoter, and preferably within the uridine diphosphate glucuronosyltransferase I (UGT1A1) promoter. The polymorphisms comprise a variation in the number of thymidine-adenine repeats, $TA_n$, where n=the number of TA repeats. Preferably the polymorphisms comprise the homozygous genotypes $[TA]_5/[TA]_5$ and/or $[TA]_8/[TA]_8$, as well as the heterozygous genotypes $[TA]_5/[TA]_6$, $[TA]_5/[TA]_7$, $[TA]_5/[TA]_8$, $[TA]_6/[TA]_8$, $[TA]_7/[TA]_8$.

The present invention also provides methods for screening individuals for variation in glucuronidation activity by detecting polymorphisms in a UGT promoter by determining the number of TA repeats in that UGT promoter. More specifically, the present invention provides methods for screening individuals for varying glucuronidation activity caused by the presence or absence of alleles $[TA]_5$, $[TA]_6$, $[TA]_7$ and/or $[TA]_8$ in the UGT1A1 promoter.

The present invention provides methods for determining or optimizing drug dosages by detecting polymorphisms in a UGT promoter by determining the number of TA repeats in the UGT promoter. More specifically, the present invention provides methods of determining optimum dosages of drugs based upon the presence or absence of alleles $[TA]_5$, $[TA]_6$, $[TA]_7$ and/or $[TA]_8$ in the UGT1A1 promoter.

In another embodiment, the present invention provides methods for determining or optimizing drug dosages by screening individuals for variation in glucuronidation activity by detecting polymorphisms in a UGT promoter by determining the number of TA repeats in the UGT promoter. More specifically, the present invention provides methods for determining optimum dosages of drugs based upon varying glucuronidation activity caused by the presence or absence of alleles $[TA]_5$, $[TA]_6$, $[TA]_7$ and/or $[TA]_8$ in the UGT1A1 promoter.

The present invention also provides methods for predicting an individual's sensitivity to xenobiotics by detecting polymorphisms in a UGT promoter by determining the number of TA repeats in that UGT promoter. More specifically, the present invention provides methods for predicting an individual's sensitivity to xenobiotics caused by the presence or absence of alleles $[TA]_5$, $[TA]_6$, $[TA]_7$ and/or $[TA]_8$ in the UGT1A1 promoter.

In another embodiment, the present invention provides methods for predicting an individuals sensitivity to xenobiotics by screening individuals for variation in glucuronidation activity by detecting polymorphisms in a UGT promoter and determining the number of TA repeats in that UGT promoter. More specifically, the present invention provides methods for predicting an individual's sensitivity to xenobiotics based upon varying glucuronidation activity caused by the presence or absence of alleles $[TA]_5$, $[TA]_6$, $[TA]_7$ and/or $[TA]_8$ in the UGT1A1 promoter.

In a preferred embodiment, the method comprises the steps of obtaining a DNA sample from an individual, amplifying the DNA comprising all or part of a UGT1 promoter which comprises the TATA box sequence upstream of the UGT1 exon 1, determining the number of TA repeats in the amplified DNA by gel electrophoresis or sequencing the amplified DNA.

Preferably the DNA is amplified using the polymerase chain reaction (PCR) using a radioactively labeled pair of nucleotide primers that are designed to amplify the region of the promoter known to regulate expression of the UGT gene.

Preferably, the DNA region correlating with expression levels of UGT is the promoter region comprising the TATA repeat sequence in which polymorphisms in the number of TA repeats has been shown to correlate with expression of the UGT gene. More preferably, the polymorphisms comprise $[TA]_5$ and/or $[TA]_8$.

The invention further comprises a kit for screening individuals to detect polymorphisms in a UGT gene promoter, the kit comprising primers for amplifying DNA in a region comprising all or part of a UGT promoter which comprises the TATA box sequence upstream of the UGT exon 1. In a preferred embodiment, the kit also contains deoxynucleoside triphosphates, buffers, labels for detecting the polymorphisms and instructions. Most preferably, the polymorphisms comprise the homozygous genotypes $[TA]_5/[TA]_5$, and/or $[TA]_8/[TA]_8$, as well as the heterozygous genotypes $[TA]_5/[TA]_6$, $[TA]_5/[TA]_7$, $[TA]_5/[TA]_8$, $[TA]_6/[TA]_8$, and $[TA]_7/[TA]_8$.

In another embodiment, the invention further comprises a kit for screening individuals for variation in glucuronidation activity by detecting polymorphisms in a UGT gene promoter, the kit comprising primers for amplifying DNA in a region comprising all or part of a UGT promoter which comprises the TATA box sequence upstream of the UGT exon 1. In a preferred embodiments, the kit also contains deoxynucleoside triphosphates, buffers, labels for detecting the polymorphisms and instructions. Most preferably, the polymorphisms comprise the homozygous genotypes $[TA]_5/[TA]_5$ and/or $[TA]_8/[TA]_8$, as well as the heterozygous genotypes $[TA]_5/[TA]_6$, $[TA]_5/[TA]_7$, $[TA]_5/[TA]_8$, $[TA]_6/[TA]_8$, and $[TA]_7/[TA]_8$.

Numerous additional aspects and advantages of the invention will become apparent to those skilled in the art upon consideration of the following detailed description of the invention which described presently preferred embodiments thereof and are not intended to limit the invention as described in the claims.

DETAILED DESCRIPTION

Hepatic glucuronidation results from the activities of a multigene family of UGT enzymes, the members of which exhibit specificity for a variety of endogenous substrates and xenobiotics. The UGT enzymes are broadly classified into two distinct gene families. The UGT1 locus codes for multiple isoforms of UGT, all of which share a C-terminus encoded by a unique set of exons 2–5, but which have a variable N-terminus encoded by different first exons, each with its own independent promoter. Bosma, et al., *Hepatology.*, 15:941–947 (1992); Ritter, et al., *J. Biol. Chem.*, 267:3257–3261 (1992). The variable first exons confer the substrate specificity on the enzyme. Isoforms of the UGT2 family are unique gene products of which at least eight isozymes have been identified. Clarke, et al. *Handbook of Experimental Pharmacology* 112:3–43 (1994). The UGT1A1 isoform is the major bilirubin glucuronidation enzyme. Genetic defects in the UGT1A1 gene can result in decreased glucuronidation activity which leads to abnormally high levels of unconjugated serum bilirubin that may enter the brain and cause encephalopathy and kernicterus. Owens & Ritter, *Progress in Nucleic Acid Research & Molecular Biology*, 51:305–338 (1995). As described above, this condition is commonly known as Gilbert's syndrome. The molecular defect in Gilbert's Syndrome is a change in the TATA box within the UGT1A1 promoter. Bosma, et al., *N. Eng. J. Med.*, 333:1171–1175 (1995); Monaghan, et al., *Lancet*, 347:578–581 (1996). This promoter usually contains a $(TA)_6TAA$ element, but another allele, termed UGT1A1*28 or allele 7, is also present in human populations at high frequencies, and contains the sequence $(TA)_7$ TAA. This polymorphism in the promoter of the UGT1A1 gene results in reduced expression of the gene and accounts for most cases of Gilbert's Syndrome. Bosma, et al., *N. Eng. J. Med.*, 333:1171–1175 (1995). As discussed below, overall, gene expression levels for the UGT1A1 promoter alleles are inversely related to the length of the TA repeat in the TATA box.

The variation observed in this promoter may also account for the inter-individual and inter-ethnic variation in drug metabolism and response to xenobiotic exposure. UGTs have been shown to contribute to the detoxification and elimination of both exogenous and endogenous compounds. For example, the examples set out below demonstrate the role of the UGT1A1 isoform in the glucuronidation of SN-38 (7-ethyl-10-hydroxycamptothecin) to the corresponding glucuronide (10-O-glucuronyl-SN-38, SN-38G) as well as the glucuronidation of TAS-103 (6-[[2-(dimethylamino)ethy]amino]-3-hydroxy-7H-indeno[2,1-c]quinoline-7-one dihydrochloride) to its corresponding glucuronide (TAS-103G). SN-38 is the active form of Irinotecan (CPT-11,7-ethyl-10-[4-(1-piperidino)-1-piperidino]carbonyloxycamptothecin), which is a camptothecin derivative used in the treatment of metastatic colorectal cancer and other malignancies. The metabolism of SN-38 and TAS-103 are merely illustrative of the present invention.

Irinotecan is biotransformed by tissue and serum carboxylesterases to an active metabolite, SN-38, which has a 100–1,000-fold higher antitumor activity than Irinotecan. SN-38 is glucuronidated by hepatic uridine diphosphate glucuronosyltransferases (UGTs) to form SN-38 glucuronide (10-O-glucuronyl-SN-38, SN-38G), which is inactive and excreted into the bile and urine although, SN-38G is sometimes deconjugated to form SN-38 by intestinal β-glucuronidase enzyme. Kaneda, et al., *Cancer Res.* 50:1715–1720 (1990).

The major dose-limiting toxicities of Irinotecan include diarrhea and, to a lesser extent, myelosuppression. Irinotecan-induced diarrhea can be serious and often does not respond adequately to conventional antidiarrheal agents. Takasuna, et al., *Folia Pharmacol. Jpn* 105:447–460 (1995). This diarrhea may be due to direct enteric injury caused by the active metabolite, SN-38, which has been shown to accumulate in the intestine after intra peritoneal administration of Irinotecan in athymic mice. Araki, et al., *Jpn. J. Cancer Res.* 84:697–702 (1993). The results of a recently completed phase I clinical trial, demonstrated that there was an inverse relationship between SN-38 glucuronidation rates and severity of diarrheal incidences in patients treated with increasing doses of Irinotecan. Gupta, et al., *Cancer Res.* 54:3723–3725 (1994). These findings indicate that glucuronidation of SN-38 protects against Irinotecan-induced gastrointestinal toxicity. A complete discussion of the correlation between diarrhea and SN-38 glucuronidation, as well as a description of biochemical methods for determining glucuronidation levels can be found in U.S. Pat. No. 5,786,344 and WO96/01127 which are both incorporated herein by reference in their entirety. Likewise, the results of studies using TAS-103 demonstrate that glucuronidation of TAS-103 may protect against TAS-103 induced toxicity. Therefore, the conversion of these two toxic compounds by hepatic UGTs demonstrates the importance of monitoring glucuronidation activity as an indicator of susceptibility to toxicity caused by exposure to compounds that are metabolized by UGTs. Furthermore, differential rates of SN-38 glucuronidation among subjects may explain the considerable inter-individual variation in the pharmacokinetic parameter estimates and toxicities observed after treatment with anti-cancer drugs or exposure to xenobiotics. Gupta, et al., *Cancer Res.* 54:3723–3725 (1994); Gupta, et al., *J. Clin. Oncol.* 15:1502–1510 (1997).

When two species (Gunn rats (Gunn, C. H., *J. Hered.*, 29:137–139 (1938)) and CN-1 patients) that are deficient in specific isoforms of UGT were screened for TAS-103 and SN-38 glucuronidation activity, there was approximately an 80% lower glucuronidation rate of TAS-103 in vitro and no in vitro glucuronidation of SN-38. These results demonstrate the role of the UGT1 family in catalyzing SN-38 and TAS-103 conjugation. Furthermore, these results demonstrate that the UGT isoform family does not play a role in the glucuronidation of SN-38. On the other hand, while the UGT1 family is the predominate isoform involved in TAS-103 glucuronidation, the UGT2 isoform family may also participate in TAS-103 glucuronidation. Failure to glucuronidate SN-38 and TAS-103 in these instances results specifically from the genetic defect in UGT1.

Other experiments, explained below, confirm the association between the UGT1A1 isoform and SN-38 and TAS-103 glucuronidation. The results described herein show that substantial genetic variability exists in the UGT1A1 isoform family and particularly in the UGT1A1 promoter. This genetic variability has been shown to correlate with gene expression. For example, the presence of the 5 allele in the UGT1A1 promoter leads to increased gene expression while the presence of the 8 allele leads to reduced gene expression. Differences in gene expression levels may give rise to individuals with varying abilities to glucuronidate compounds metabolized by UGT. This prediction was confirmed through a correlation analysis of UGT1A1 promoter genotype and rate of in vitro SN-38 and TAS-103 glucuronidation.

It follows therefore that individuals with the 8 allele may also have differing susceptibility to xenobiotics when compared to other genotypes when those compounds are metabolized by UGTs. On the other hand, the presence of the 5 allele that correlates with increased gene expression and higher glucuronidation activity may result in the administration of less than optimum drug dosages. For example, when a drug metabolized by UGTs is administered to an individual with this polymorphism, the increased glucuronidation activity may cause more of the drug to be converted into the inactive metabolite in a shorter period, thereby reducing the drug's effectiveness. Conversely, in the rare case of drugs and xenobiotics that require glucuronidation for activation, decreased glucuronidation activity may cause less of the activated form of the drug or xenobiotic to be available.

The fact that repeated sequences are intrinsically unstable and tend to lengthen and shorten as a result of unequal crossing-over during meiosis may explain the presence of other alleles, in addition to $[TA]_6$ and $[TA]_7$, in the population. The examples below describe two additional alleles identified in human populations: allele 5, containing the sequence $[TA]_5TAA$ and allele 8, containing the sequence $[TA]_8TAA$. Interestingly, alleles 5 and 8 were found in population samples from Sub-Saharan Africa, where they occur at lower frequencies than the common alleles 6 and 7 although it is possible that these two alleles are present across a variety of ethnic groups. The frequency of allele 6 and 7 also appears to differ significantly across ethnic groups, with Asian and Amerindian populations showing the highest frequencies of allele 6. Conversely, alleles 6 and 7 occur at intermediate and similar frequencies among Caucasians and Sub-Saharan Africans.

Several hypotheses may be proposed regarding the selective pressures that might be responsible for the observed pattern of inter-population variation at the UGT1A1 promoter. It was previously proposed that the maintenance of intermediate levels of bilirubin is adaptive, Beutler, et al., *Proc. Natl. Acad. Sci. USA*, 95:8170–8174 (1998), and that the alleles at this promoter would be maintained in the population by balancing selection. This hypothesis is based on the observation that bilirubin is a potent antioxidant likely to have physiological significance. Stocker, et al., *Science*, 235:1043–1046 (1987). However, it is also known that glucuronidation is an important detoxification step for many endogenous as well as exogenous compounds. Clarke & Burchell, *Handbook of Experimental Pharmacology*, FC Kaufman Ed., Berlin/Heidelberg:Springer-Verlag, p. 3–43 (1994). In addition to TAS-103 and SN-38, UGT1A1 is likely to act on other substrates present in the environment, e.g., dietary components, environmental pollutants and carcinogens, which require detoxification as well as playing a role in the metabolism of bilirubin and other endogenous compounds. Within this framework, maintaining high levels of UGT1A1 gene expression would ensure rapid elimination of toxic or endogenous compounds and be advantageous.

As described herein, the correlation between in vitro glucuronidation rate and UGT1A1 promoter polymorphism found for alleles 6 and 7 has been shown to extend to alleles 5 and 8. Because these alleles appear to be present in subsets of human populations (for example, those of African origin), an even higher inter-individual variability in SN-38 and TAS-103 metabolism might be expected within these populations. Because the inverse relationship between TA repeat size and rate of SN-38 glucuronidation extends to alleles 5 and 8, a screening assay that identifies these alleles can facilitate individualization of drug therapy, identify individuals susceptible to xenobiotic exposure, and can be used to improve drug dosage calculations.

The examples set forth below are intended to be illustrative of the present invention and are not intended to limit the scope of the invention as set out in the appended claims.

Example 1 describes an SN-38 glucuronidation assay using liver microsomes from normal rats, normal humans, Gunn rats and CN-1 patients. Example 2 describes a 3'-azido-3'-deoxythymidine (AZT) glucuronidation assay used as a control. Example 3 describes correlation studies with in vitro SN-38 glucuronidation versus bilirubin and PNP glucuronidation in human liver microsomes. Example 4 describes an experiment designed to measure SN-38 glucuronidation by cDNA-expressed isoforms of UGT. Example 5 describes correlation studies with in vitro TAS-103 glucuronidation versus bilirubin and SN-38 glucuronidation. Example 6 describes the relationship between UGT1A1 promoter genotype and SN-38 glucuronidation. Example 7 describes non-limiting examples of diagnostic applications of the methods for screening for UGT1A1 genotype.

EXAMPLE 1

SN-38 Glucuronidation Assay

To investigate which UGT enzymes are responsible for SN-38 glucuronidation, the in vitro metabolism of SN-38 was measured using normal human and rat liver microsomes, as well as microsomes from Gunn rats, Gunn, C. H., *J. Hered.*, 29:137–139 (1938), and patients with Crigler-Najjar type I (CN-1) syndrome. Liver microsomes were prepared from normal humans, CN-1 patients, normal rats, and Gunn rats and assayed for SN-38 glucuronidation. Microsomes from human liver samples medically unsuitable for liver transplantation were acquired under the auspices of the Washington Regional Transplant Consortium. In addition, microsomes were prepared by differential centrifugation methods. Purba, H. S., et al., *Br. J. Clin. Pharmaocol.* 23:447–453, using human liver samples obtained with the approval of the Institutional Review Boards of institutions involved through the Liver Tissue Procurement and Distribution System. Investigations were performed with pooled microsomes from normal rats, normal humans and Gunn rats, while microsomes from CN-1 patients were used individually.

Microsomes (1 mg/ml) were incubated with SN-38 (5 $\mu$M), $MgCl_2$ (10 mM), and UDPGA (5 mM) in a 0.1 M Tris-HCl buffer medium (pH 7.4) for 30 minutes at 37° C., in a final volume of 200 $\mu$l. After stopping the reaction with 400 $\mu$l methanol, the incubation mix was centrifuged at 2,500 rpm for 30 minutes at 4° C. The supernatant was evaporated to dryness under nitrogen and in preparation of analysis by high pressure liquid chromatography (HPLC), the supernatant was reconstituted with 250 $\mu$l of a mobile phase consisting of 35% acetonitrile and 65% 0.1 M $KH_2PO_4$ containing 3 mM sodium heptane sulphonate (pH 4.0), used at a flow rate of 0.8 ml/min. A $C_{18}\mu$ Bondapak column (10 $\mu$m, 3.9×300 mm) was used with fluorescence detection at the following wavelengths: 355 nm and 515 nm. 100 $\mu$l aliquots of the reconstituted supernatant were injected into an HPLC assay system. CPT was used as the internal standard. The chromatographs obtained after in vitro glucuronidation of normal human and rat microsomes revealed three peaks corresponding to SN-38G, SN-38, and CPT. Retention times were approximately 3.5, 9, and 10 minutes, respectively. The peaks for each of these compounds were confirmed using standards of SN-38G, SN-38, and CPT.

Inter-individual variations in rates of SN-38 glucuronidating activity were evaluated by screening 25 normal human liver microsomes for in vitro SN-38 glucuronidation activity. There was considerable variation in the rates of SN-38G formation among individuals, with a range of 0.5–26 pmol of SN-38G formed/min/mg microsomal protein.

Chromatographs obtained after in vitro glucuronidation of CN-1 patients and Gunn rats revealed Only two peaks corresponding to SN-38 and CPT. Retention times for SN-38 and CPT were approximately 9 and 10 minutes, respectively. The absence of the peak at approximately 3.5 minutes indicates that microsomes from both CN-1 patients and Gunn rats lack SN-38 glucuronidating activity.

EXAMPLE 2

AZT Glucuronidation Assay

To ensure the viability and functional enzymatic activity of the microsomal preparations, the UGT activity toward another substrate, AZT (3'-azido-3'-deoxythymidine) was investigated as a control. Liver microsomes from normal humans, CN-1 patients, normal rats, and Gunn rats were prepared as described above. Investigations were performed in pooled microsomes from normal rats, normal humans and Gunn rats, while microsomes from CN-1 patients were used individually.

Microsomes were preincubated with oleolyl lysophosphatidylcholine (OLPC) (0.8% wt/wt. OLPC/microsomal protein) at 4° C. for 20 minutes. The final reaction mixture contained 1 mg/ml preincubated microsomes, AZT (5 mM), $MgCl_2$ (10 mM), 0.2 M Tris-HCl buffer (pH 7.3), and UDPGA (10 mM) in a final volume of 300 $\mu$l. After an incubation period of 1 hour at 37° C., the reaction was stopped with the addition of 30 $\mu$l of HCl. Proteins were removed after centrifugation at 10,500 g for 5 minutes and 30 $\mu$l aliquots of the supernatant were subjected to HPLC analysis and the metabolites were detected in an ultraviolet detector at a wavelength of 265 nm. The mobile phase consisted of a 15:85 mixture of acetonitrile/ammonium phosphate buffer (0.1% vol/vol phosphoric acid, adjusted to pH 2.7 with ammonium hydroxide) used at a flow rate of 1 ml/min. Intact in vitro formation of G-AZT was observed in microsomes from all four sources.

Using the HPLC conditions described above, UDPGA/ UDP (coelution), G-AZT, and AZT eluted at approximately 2.6, 5.7 and 9.5 minutes, respectively. These peaks appeared consistently after incubation of AZT with microsomes from normal rats and humans as well as in Gunn rats and CN-1 patients. The retention times obtained were confirmed using standard solutions of the respective chemicals.

EXAMPLE 3

Glucuronidation Correlation Assay

To determine which UGT1 isoform is responsible for SN-38 glucuronidation, the correlation between the rates of formation of SN-38G and glucuronidation of bilirubin & PNP was investigated. PNP was chosen because planar phenols such as PNP and acetaminophen are glucuronidated predominantly by UGT1A6, See Burchell, et al., *DNA cell biol.*, 10:487–494 (1991); Harding, et al., *Proc. Natl. Acad. Sci. USA*, 85:8381–8385 (1988), although several other isoforms such as UGT1A1, UGT1A4, and UGT2B15 have been reported to play a role in PNP glucuronidation in humans. See King, et al., *Arch. Biochem. Biophys.*, 332:92–100 (1996); Green, et al., *Drug Metab. Dispos.*, 23:299–302 (1995). Bilirubin was chosen because bilirubin has been previously shown to be glucuronidated by two isozymes of UGT1: UGT1A1 and UGT1A4. Ritter, et al., *J. Biol. Chem.*, 266:1043–1047 (1991).

The formation of bilirubin mono- and diglucuronides was quantified using $^{14}$C-labeled UDPGA as follows. Human liver microsomes (0.5 mg/ml) were incubated with bilirubin (0.343 mM), L-α-phosphatidylcholine (0.75 mg/ml), saccharolactone (8.5 mM), $MgCl_2$ (10 mM), and [$^{14}$C]UDPGA (5 mM) in a 0.5 M Tris-HCl medium (pH 7.4) for 60 minutes at 37° C., in a final volume of 100 µl. The reaction was stopped with 100 µl of 0.7 M glycine-HCl buffer (pH 2.0). Radiolabeled bilirubin glucuronides were extracted into ethyl acetate (1 ml), and the radioactivity in 300 µl aliquots was measured using a liquid scintillation counter.

The formation of glucuronidated PNP was quantified by the following method. A preincubated (4° C. for 30 minutes) mixture of human liver microsomes (1 mg/ml) with Triton X-100 (0.025% vol/vol) was incubated (final volume 200 µl) with PNP (360 µM), EDTA (40 µM), $MgCl_2$ (10 mM), UDPGA (2 mM) in a 0.1 M Tris-HCl buffer (pH 7.4) for 10 minutes at 37° C. The reaction was stopped by the addition of 2.8 ml of 0.2 M glycine-NaOH buffer (pH 10.4). Samples were centrifuged at 2,500 rpm for 30 minutes, and UGT activity in the supernatant was analyzed colorimetrically in a spectrophotometer by measuring the disappearance of the substrate at a wavelength of 400 nm.

Figure 1:
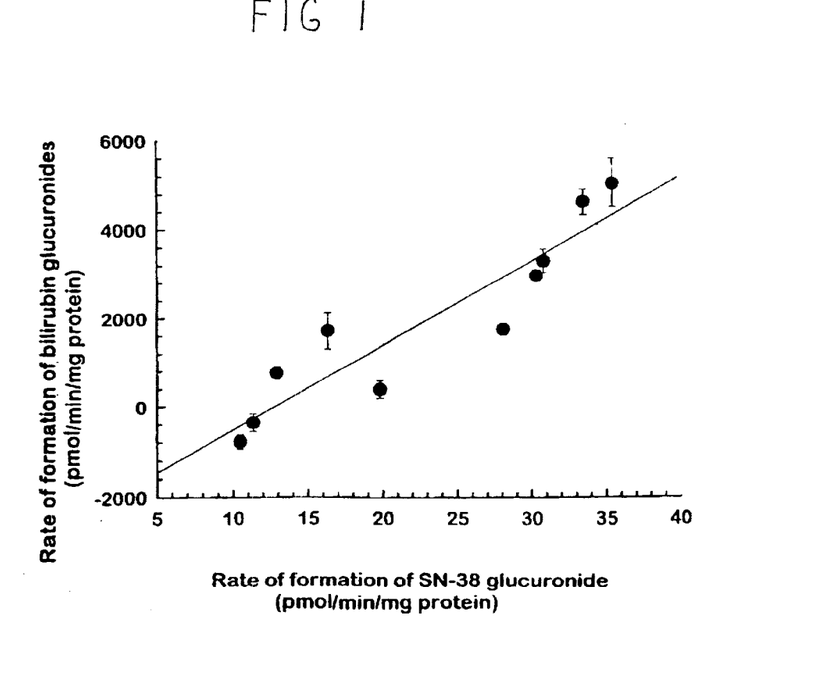
FIG. 1 displays correlation assay data demonstrating the correlation between in vitro SN-38 and bilirubin glucuronidation in human liver microsomes. Each data point represents the mean of three separate determinations.

There was a significant correlation between rates of formation of SN-38G and bilirubin mono- and diglucuronides as shown in FIG. 1. (Pearson correlation coefficient, r=0.89, P=0.0001). In contrast, there was a poor association between SN-38G formation and PNP glucuronidation (r)= 0.08, P=0.703). The rates of PNP glucuronidation were distributed evenly among subjects (mean±SEM 20.39±2.4, range 16.48–23.82 nmol PNP glucuronidated/min/mg protein. The similarity between SN-38 and bilirubin glucuronidation suggests that bilirubin UGT may also be glucuronidating SN-38.

EXAMPLE 4

SN-38 Glucuronidation by cDNA-expressed Isoforms of UGT

To determine which particular isozyme of UGT1 glucuronidates SN-38, HK293 cells transfected with and expressing cDNA encoding selected UGT1 isozymes and a member of the UGT2 family (UGT2B7) were screened for SN-38 glucuronidating activity. Culture media and conditions for stable expression of human UGT1A1, UGT1A4, and UGT2B7 have been described previously. Coffman, et al., *Mol. Pharmacol.*, 47:1101–1105 (1995), Green, et al., *Drug Metab. Dispos.*, 23:299–302 (1995); Coffman, et al., *Drug Metab. Dispos.*, 25:1–4 (1997) all are incorporated herein by reference. Briefly, the XbaI/XhoI and BamHI-XhoI fragments of human UGT1A1, UGT1A4, and UGT2B7 were subcloned into the respective corresponding sites of the mammalian expression vectors pcDNA3, pREP9, and pcDNA3.1. HK293 cells were transfected with the vector-UGT isozyme using the calcium phosphate transfection method. Chen, et al., *Biotechniques*, 6:632–638 (1988). The cells were then assayed for glucuronidation activity as described above.

Figure 2:
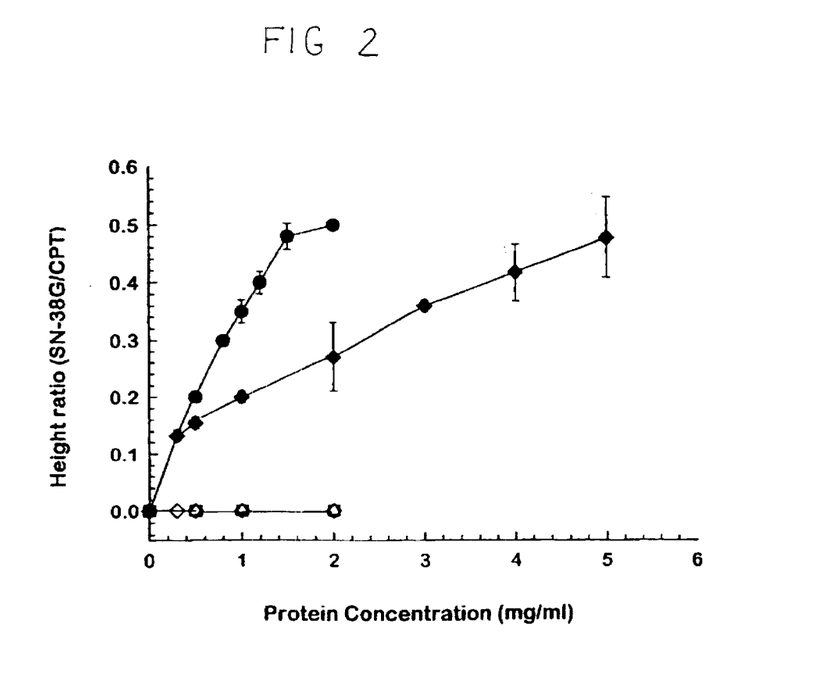
FIG. 2 displays glucuronidation assay data demonstrating in vitro glucuronidation of SN-38 by cDNA-expressed UGT isoforms. Cell lysates from HK293 cells expressing UGT1A1 (♦), UGT1A4 (□) and UGT2B7 enzymes (∆), and membrane preparations of HK293 cells expressing UGT1A1 enzyme (●), were screened for SN-38 glucuronidating activity. HK293 cells (◊) were used as a control. Each data point represents the mean of three separate determinations.

These experiments resulted in a clear demonstration of the role of UGT1A1 in glucuronidating SN-38 as shown in FIG. 2. There was a lack of SN-38 glucuronidating activity in control HK293 cells and those expression UGT1A4 and UGT2B7, up to a protein concentration of 2 mg/ml. On the other hand, there was measurable SN-38G formation in cells expressing UGT1A1, which increased with increasing protein concentrations. The high correlation between SN-38 and bilirubin glucuronidation suggests that UGT1A1 is the isoform involved in SN-38 glucuronidation.

EXAMPLE 5

Correlation Between Rates of Formation of TAS-103G, SN-38G, and Glucuronidated Bilirubin In an effort to demonstrate that UGT1A1 also plays a role in glucuronidation of other toxic compounds, the correlation between rates of formation of TAS-103G, SN-38G and glucuronidation of bilirubin was investigated. Microsomes (protein=2 mg/ml) were obtained from liver samples from different species: human, rat, mice and ferrets. Microsomes were incubated with TAS-103 (80 µM), $MgCl_2$ (10 mM), and UDPGA (2 mM) in 0.1 M Tris-HCl buffer (pH 7.4) for 20 minutes at 37° C. Retention times of about 6, 9, and 15 minutes were obtained for TAS-103G, TAS-103, and TAS-1-018 (internal standard), respectively, after HPLC separation and UV (460 nm) detection.

There were extensive inter-subject differences in the rates of TAS-103 glucuronidation [mean area ratio of TAS-103G/ TAS-1-018 peaks=11.2±5.9 (SD), range=1.02 to 27.26] in normal liver microsomes (n=18). TAS-103 glucuronidation rates correlated significantly with the glucuronidation of SN-38 (the active metabolite of Irinotecan, (Pearson r=0.94, P<0.01) and bilirubin (r)=0.82, P<0.01), suggesting the involvement of UGT1A1 and/or UGT1A4 isoforms.

The role of UGT1A1 was confirmed using microsomes from lymphoblast cells that were specifically transfected with cDNA expressing UGT1A1, UGT1A4, and UGT1A6 isoforms. TAS-103G formation was observed only in microsomes containing UGT1A1 enzymes (mean area ratio=7.18). No TAS-103 glucuronidating activity was observed in microsomes containing UGT1A4, UGT1A6, or in control lymphoblasts. Microsomes from Gunn rats and CN-1 patients that lack bilirubin and SN-38 UGT activity exhibited intact, but low glucuronidating activity (Gunn rats: 3.32±0.94; CN-1 patients: 2.75±0.11), indicating that one or more of the UGT2 isoforms are also involved in TAS-103 glucuronidation. Even so, these findings indicate that TAS-103 is glucuronidated predominantly by UGT1. Therefore, individuals with decreased UGT1A1 activity, such as those with Gilbert's Syndrome, may be at an increased risk for toxicity induced by exposure to compounds metabolized by UGTs.

EXAMPLE 6

Relationship Between UGT1A1 Promoter Genotype and SN-38 Glucuronidation

The experiments described below demonstrate a significant correlation between UGT1A1 promoter genotype and rates of bilirubin and SN-38 glucuronidation in liver tissue samples, as well as the genetic role of UGT1A1 polymorphism in the metabolism of Irinotecan. SN-38 and bilirubin glucuronidation assays were performed in human liver microsomes. Four promoter alleles were found at the UGT1A1 locus: $[TA]_6TAA$ and $[TA]_7TAA$ which have been well characterized and two new polymorphisms, $[TA]_5TAA$ and $[TA]_8TAA$. $[TA]_6TAA$ is the wild-type allele known to be associated with bilirubin levels within the normal range. $[TA]_7TAA$ is known to be associated with Gilbert's Syndrome phenotype which is characterized by reduced levels of gene expression and therefore reduced glucuronidation activity resulting in higher levels of bilirubin. As the following experiment illustrates, the presence of a longer TATA element, $[TA]_7$ or $[TA]_8$, in the promoter region of the gene for bilirubin UDP-glucuronosyltransferase results in reduced expression of the gene and therefore, reduced glucuronidation activity resulting in higher SN-38 levels. Reduced glucuronidation activity is a signal that a genetic predisposition to toxicity may exist. In contrast, the presence of a shorter TATA element, $[TA]_5$, in the promoter region of the gene for bilirubin UDP-glucuronosyltransferase results in increased expression of the gene and therefore, increased glucuronidation activity resulting in lower SN-38 levels.

DNA isolated from caucasian livers was subjected to polymerase chain reaction and size differentiating gel electrophoresis. The variability in the number of TA repeats at the UGT1A1 promoter was genotyped as previously described by Monaghan, et al., Lance, 347:578–581 (1996) using polymerase chain reaction (PCR). Primer pairs A/B (SEQ ID NOs: 3 & 4) or C/D (SEQ ID NOs: 1 & 2) were used to amplify fragments of 253–255 base pairs and 98–100 base pairs, respectively. Amplifications were in 0.2 nmol/L of the four deoxynucleoside triphosphates (dATP, dCTP, dGTP, dTTP), 50 nmol/L of KCl, 10 nmol/L Tris-HCl (pH 9.0 at 25° C.), 0.1% Triton X-100®, 1.5 nmol/L $MgCl_2$, 0.25 μmol/L of each primer, 1 unit of Taq polymerase (Promega), and human genomic DNA (0.25–0.50 μg). The Perkin-Elmer Cetus DNA thermal cycler was used for the reactions and PCR conditions were: 95° C. for 5 minutes followed by 30 cycles of 95° C. for 30 seconds, 58° C. for 40 seconds, and 72° C. for 40 seconds.

Amplification was confirmed before direct sequencing by agarose gel electrophoresis with $[\alpha^{-35}S]$-dATP and the USB Sequenase PCR product sequencing kit. Sequenced products were resolved in 6% denaturing polyacrylamide gels. The dried gels were exposed overnight to autoradiographic film before being developed.

Radioactive PCR was also used and in that case, amplification was done as described above using primer pair C/D (SEQ ID NOs: 1 & 2) except that 2.5 pmol of primer C (SEQ ID NO: 1) was first radioactively 5' end-labeled with 2.5 μCi of $[\gamma^{-32}P]$-ATP. Products were resolved on 6% denaturing polyacrylamide gels and the wet gels were exposed to autoradiographic film (−70° C. for 15 minutes) before being developed.

The three possible genotypes, determined by amplification/sequencing or radioactive PCR, were homozygosity for the common allele (6/6), heterozygosity (6/7) or homozygosity for the rarer allele (7/7).

In order to investigate the variability at the UGT1A1 promoter across ethnic groups, 11 samples drawn at random from aboriginal and admixed populations from different ethnic backgrounds were genotyped. The results, shown in Table 1 below, indicate that four alleles are present in human populations and their frequencies vary considerably across ethnic groups.

TABLE 1

GENOTYPE & ALLELE FREQUENCIES AT THE UGT1A1 PROMOTER IN UNSELECTED POPULATIONS

| POPULATION | GENOTYPE FREQUENCY (%) | | | | | | | ALLELE FREQUENCY (%) | | | | N | HWE |
|---|---|---|---|---|---|---|---|---|---|---|---|---|---|
| | 5/6 | 5/7 | 6/6 | 6/7 | 6/8 | 7/7 | 7/8 | 5 | 6 | 7 | 8 | | |
| Sub-Saharan Africans | | | | | | | | | | | | | |
| Bamileke' (Cameroon) | 8 | 13 | 13 | 38 | 13 | 17 | 0 | 10 | 42 | 42 | 6 | 24 | ns |
| Pygmy Mbenzele (Cameroon) | 2 | 5 | 10 | 36 | 10 | 33 | 5 | 4 | 33 | 56 | 7 | 42 | ns |
| Ewondo (Cameroon) | 10 | 10 | 30 | 50 | 0 | 0 | 0 | 10 | 60 | 30 | 0 | 10 | ns |
| Asians | | | | | | | | | | | | | |
| Japanese | 0 | 0 | 84 | 15 | 0 | 1 | 0 | 0 | 91 | 9 | 0 | 67 | ns |
| Chinese | 0 | 0 | 65 | 31 | 0 | 4 | 0 | 0 | 80 | 20 | 0 | 23 | ns |
| Caucasians | | | | | | | | | | | | | |
| Bedouin (Saudi Arabia) | 0 | 0 | 56 | 28 | 0 | 17 | 0 | 0 | 69 | 31 | 0 | 18 | ns |
| Sardinians | 0 | 0 | 56 | 36 | 0 | 9 | 0 | 0 | 74 | 26 | 0 | 70 | ns |

TABLE 1-continued

GENOTYPE & ALLELE FREQUENCIES AT THE UGT1A1 PROMOTER IN UNSELECTED POPULATIONS

| POPULATION | GENOTYPE FREQUENCY (%) | | | | | | | ALLELE FREQUENCY (%) | | | | N | HWE |
|---|---|---|---|---|---|---|---|---|---|---|---|---|---|
| | 5/6 | 5/7 | 6/6 | 6/7 | 6/8 | 7/7 | 7/8 | 5 | 6 | 7 | 8 | | |
| Amerindians | | | | | | | | | | | | | |
| Kaingang (Brazil) | 0 | 0 | 80 | 18 | 0 | 2 | 0 | 0 | 89 | 11 | 0 | 50 | ns |
| Guarani' (Brazil) | 0 | 0 | 68 | 26 | 0 | 6 | 0 | 0 | 81 | 19 | 0 | 31 | ns |
| Admixed | | | | | | | | | | | | | |
| Hispanics | 0 | 2 | 41 | 41 | 0 | 16 | 0 | 1 | 61 | 38 | 0 | 44 | ns |

In addition to the common alleles 6 and 7, alleles that differ in fragment length from 6 and 7 by −2 and +2 base pairs, respectively were detected. These alleles were amplified and directly sequenced as described above and shown to contain [TA]$_5$TAA and [TA]$_8$TAA TA repeats, respectively. Alleles [TA]$_5$TAA and [TA]$_8$TAA were found in population samples from Sub-Saharan Africa, were they occur at lower frequencies compared to the common alleles [TA]$_6$TAA and [TA]$_7$TAA. The finding of a Hispanic individual carrying allele [TA]$_5$TAA is likely due to genetic admixture with African Americans.

To investigate whether alleles [TA]$_5$TAA and [TA]$_8$TAA affected glucuronidation activity, 15 additional liver samples, collected from African Americans, were genotyped at the UGT1A1 promoter as described above. To determine the sequences of alleles [TA]$_5$TAA and [TA]$_8$TAA, primers A and B (SEQ ID NOs: 3 and 4, respectively) were used for both PCR and cycle sequencing. The amplification product was purified by using the QIAquick PCR purification kit and directly sequenced using the BigDye™ Terminator cycle Sequencing Ready Reaction kit and an ABI 377 automated sequencer.

Microsomes (1 mg/ml) were obtained from human liver tissue samples and were incubated with SN-38 (5 μM), MgCl$_2$ (10 mM), and UDPGA (5 mM) in a 0.1 M Tris-HCl buffer medium (pH 7.4) for 30 minutes at 37° C., in a final volume of 200 μl. SN-38, SN-38G and the internal standard, CPT, were separated using high performance liquid chromatography (HPLC) coupled to fluorescence detection ($_{ex}$= 355 nm and $_{em}$=515 nm). SN-38 reaction rates were linear for incubation times up to at least 1.5 hours and for final protein concentrations of up to 2 mg/ml. The results of this analysis, shown in Table 2 below, also include the liver samples of Caucasian origin from the first study. A significant trend toward a decrease in mean glucuronidation rate between genotype groups is observed (p<0.01, nonparametric trend analysis), except for the 6/8 and 7/7 groups. Statistical analysis using the sum of alleles in a individual's genotype (instead of genotypes) indicated a significant difference between livers with allele sums 11 & 12 (corresponding to genotypes 5/6, 5/7 and 6/6) and 13 & 14 (corresponding to genotypes 6/7, 6/8, and 7/7) (p<0.01).

TABLE 2

| Sample | | UGT1A1 Promoter Genotype | | | | | |
|---|---|---|---|---|---|---|---|
| | | 5/6 | 5/7 | 6/6 | 6/7 | 6/8 | 7/7 |
| Caucasians | N (%) | 0 (0) | 0 (0) | 15 (56) | 9 (33) | 0 (0) | 3 (11) |
| | M {SE} | | | 0.36 {0.03} | 0.25 {0.03} | | 0.09 {0.01} |
| African Americans | N (%) | 3 (20) | 1 (7) | 2 (13) | 5 (33) | 1 (7) | 3 (20) |
| | M {SE} | 0.41 {0.1} | 0.39 | 0.32 {0.01} | 0.25 {0.03} | 0.12 | 0.12 {0.07} |

M = mean SN-38 glucuronidation rate (ratio measured as: peak area of SN-38 glucuronide ÷ peak area CPT, where CPT = internal standard).
SE = standard error To evaluate the functional viability of microsomal drug-metabolizing enzymes in the liver samples used in this study, the livers were screened for 7-ethoxycoumarin O-deethylation, as 7-ethoxycoumarin is oxidized to umbelliferone by multiple cytochrome P450 enzymes. The method used is described by Evans & Relling, *J. Chromatogr.*, 578:141–145 (1992). Rates of umbelliferone formation were within the expected range, indicating normal cytochrome P450 activity in these liver samples.

EXAMPLE 7

Diagnostic and Screening Applications

The findings described above which show the correlation between a polymorphism in the promoter of a UGT gene and levels of gene expression may be used in a number of different assays. For example, the methods described above can be used in diagnostic or screening assays wherein individuals are screened for the predisposition to drug and chemical sensitivity exhibited by individuals with varying levels of hepatic uridine diphosphate glucuronosyltransferases (UGTs).

In view of the fact that a significant number of cases of toxicity due to administration of drugs are caused by low levels of hepatic uridine diphosphate glucuronosyltransferases (UGTs) that can be traced to the presence of a longer TATA element, [TA]$_7$ or [TA]$_8$, in the promoter region of the gene for bilirubin UDP-glucuronosyltransferase, a diagnostic application that identifies this genetic polymorphism is quite useful. Therefore, in one embodiment, the genotype of the UGT1A1 promoter is determined as described in Example 6. After screening for any of the polymorphism, the amount of drug administered should be adjusted to avoid drug induced toxicity or to optimize the therapeutic dose of the drug.

Additionally, the methods described above are useful when an individual has a genotype that includes the presence of allele [TA]$_5$. In a second embodiment, the genotype of the UGT1A1 promoter is determined as described in example 6. Specifically, the presence of allele [TA]$_5$ is confirmed. A certain percentage of potential chemotherapy patients (particularly those of Sub-Saharan African descent) may be expected to have this genotype as compared to normal subjects. The drug dose administered to these individuals may have to be increased to achieve maximum effectiveness. The presence of allele [TA]$_5$ is an indication that the individual has higher than normal glucuronidation activity which may lead to inactivation of the drug metabolites and excretion of a greater percentage of the drug administered. On the other hand, in a case where a drug requires glucuronidation for activation, dosages may require adjusting to compensate for the increased level of activation caused by the presence of allele [TA]$_5$.

In addition to the previously described anti-cancer drugs, oral contraceptives provide another situation in which individuals with a UGT polymorphism may suffer clinical manifestations because of improper drug dosages. Women with genotypes that include alleles [TA]$_7$, and/or [TA]$_8$ may be more susceptible to drug toxicity when taking acetaminophen and ethinyloestradiol concurrently. Since both drugs are primarily glucuronidated by the UGT1 isoform, combining them may lead to drug toxicity because of increased bioactivation of acetaminophen. In this method, the genotype is determined as described in Example 6. After determining the genotype of the individual's UGT1A1 promoter, proper drug dosages can be calculated and unnecessary cases of drug toxicity can be avoided.

Not only are the methods described above useful in the context of screening for drug sensitivity, they are also useful in a screening assay to identify individuals who have a genetic polymorphism causing sensitivity to compounds found in the environment. A certain percentage of the population may be expected to have at least one copy of the [TA]$_5$ or [TA]$_8$ allele. These individuals will exhibit differential sensitivity to xenobiotics based upon their genotype. In a third embodiment, the genotype of the UGT1A1 promoter is again determined as described in Example 6. Individuals identified as having a genotype that includes allele [TA]$_5$ can be selected when a low sensitivity to xenobiotics is required. For example, individuals working in situations where they are exposed to chemicals could be screened as a rational basis for predicting the likelihood of developing clinical manifestations as a result of chemical exposure. Individuals with genotypes including alleles [TA]$_7$ and/or [TA]$_5$ will exhibit increasing sensitivity when exposed to environmental xenobiotics because of reduced glucuronidation activity.

In another diagnostic assay based upon the methods described above, it is possible to identify individuals who have a reduced ability to metabolize endogenous compounds because of reduced glucuronidation activity. The genotype of the UGT1A1 promoter is again determined as described in Example 6. Individuals with genotypes including alleles [TA]$_7$ and/or [TA]$_8$ may exhibit clinical manifestations of their inability to conjugate and excrete endogenous compounds.

Also contemplated with the above embodiments of methods of screening for individuals predisposed to drug or chemical sensitivities are diagnostic kits for the determination of genotype of the UGT1A1 promoter. The diagnostic kits may comprise appropriate primers, deoxynucleoside triphosphates; buffers for amplification; labels for the detection of the alleles of interest; and instructions for use of said diagnostic kits.

We claim:

1. A method for detecting polymorphisms in a uridine diphosphate glucuronosyl transferase (UGT) gene promoter comprising determining the presence of eight (TA) repeats in said promoter.

2. The method of claim 1 comprising the steps of:
   (a) obtaining DNA from an individual;
   (b) amplifying all or part of said UGT1A1 gene promoter contained in said DNA; and
   (c) determining the number of TA repeats in said promoter.

3. The method of claim 1 or 2 wherein said promoter is the UGT1A1 promoter.

4. The method of claim 3 wherein said DNA being amplified comprises all or part of a UGT1A1 promoter.

5. The method of claim 1 wherein said DNA is amplified by the polymerase chain reaction (PCR) and said number of TA repeats is determined by gel electrophoresis.

6. The method of claim 1 wherein said DNA is amplified by PCR and said number of TA repeats is determined by sequencing said amplified DNA.

7. The method of claim 1 wherein said promoter has a genotype selected from the group consisting of $[TA]_5/[TA]_5$, $[TA]_5/[TA]_6$, $[TA]_5/[TA]_7$, $[TA]_5/[TA]_8$, $[TA]_6/[TA]_6$, $[TA]_6/[TA]_7$, $[TA]_6/[TA]_8$, $[TA]_7/[TA]_7$, $[TA]_7/[TA]_8$, and $[TA]_8/[TA]_8$.

8. A method for detecting polymorphisms in a uridine diphosphate glucuronosyltransferase I (UGT1A1) gene promoter comprising determining the presence of eight (TA) repeats in said promoter.

9. The method of claim 8 comprising the steps of:
   (a) obtaining DNA from an individual;
   (b) amplifying all or part of said UGT gene promoter contained in said DNA; and
   (c) determining the number of TA repeats in said promoter.

10. The method of claim 8 wherein said DNA being amplified comprises all or part of a UGT1A1 promoter.

11. The method of claim 8 wherein said DNA is amplified by polymerase chain reaction (PCR) and said number of TA repeats is determined by gel electrophoresis.

12. The method of claim 8 wherein said DNA is amplified by PCR and said number of TA repeats is determined by sequencing said amplified DNA.

13. The method of claim 8 wherein said promoter has a genotype selected from the group consisting of $[TA]_5/[TA]_5$, $[TA]_5/[TA]_6$, $[TA]_5/[TA]_7$, $[TA]_5/[TA]_8$, $[TA]_6/[TA]_6$, $[TA]_6/[TA]_7$, $[TA]_6/[TA]_8$, $[TA]_7/[TA]_7$, $[TA]_7/[TA]_8$, and $[TA]_8/[TA]_8$.

14. A method for screening individuals for variation in glucuronidation activity comprising detecting polymorphisms in a uridine diphosphate glucuronosyltransferase (UGT) gene promoter comprising determining the presence of eight (TA) repeats in said promoter.

15. The method of claim 14 comprising the steps of:
   (a) obtaining DNA from an individual;
   (b) amplifying all or part of said UGT gene promoter contained in said DNA; and
   (c) determining the number of TA repeats in said promoter.

16. The method of claim 14 or 15 wherein said promoter is the UGT1A1 promoter.

17. The method of claim 16 wherein said DNA being amplified comprises all or part of a UGT1A1 promoter.

18. The method of claim 14 wherein said DNA is amplified by the polymerase chain reaction (PCR) and said number of TA repeats is determined by gel electrophoresis.

19. The method of claim 14 wherein said DNA is amplified by PCR and said number of TA repeats is determined by sequencing said amplified DNA.

20. The method of claim 14 wherein said promoter has a genotype selected from the group consisting of $[TA]_5/[TA]_5$, $[TA]_5/[TA]_6$, $[TA]_5/[TA]_7$, $[TA]_5/[TA]_8$, $[TA]_6/[TA]_6$, $[TA]_6/[TA]_7$, $[TA]_6/[TA]_8$, $[TA]_7/[TA]_7$, $[TA]_7/[TA]_8$, and $[TA]_8/[TA]_8$.

21. A method for screening individuals for variation in glucuronidation activity comprising detecting polymorphisms in a uridine diphosphate glucuronosyltransferase I (UGT1A1) gene promoter, the method comprising determining the presence of eight (TA) repeats in said promoter.

22. The method of claim 21 comprising the steps of
   (a) obtaining DNA from an individual;
   (b) amplifying all or part of said UGT gene promoter contained in said DNA; and
   (c) determining the number of TA repeats in said promoter.

23. The method claim 21 wherein said DNA being amplified comprises all or part of a UGT1A1 promoter.

24. The method of claim 21 wherein said DNA is amplified by polymerase chain reaction (PCR) and said number of TA repeats is determined by gel electrophoresis.

25. The method of claim 21 wherein said DNA is amplified by PCR and said number of TA repeats is determined by sequencing said amplified DNA.

26. The method of claim 21 wherein said promoter has a genotype selected from the group consisting of $[TA]_5/[TA]_5$, $[TA]_5/[TA]_6$, $[TA]_5/[TA]_7$, $[TA]_5/[TA]_8$, $[TA]_6/[TA]_6$, $[TA]_6/[TA]_7$, $[TA]_6/[TA]_8$, $[TA]_7/[TA]_7$, $[TA]_7/[TA]_8$, and $[TA]_8/[TA]_8$.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
gtcacgtgac acagtcaaac                                                  20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic Primer

<400> SEQUENCE: 2
tttgctcctg ccagaggtt                                                   19

-continued

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
aagtgaactc cctgctacct t                                          21
```